(12) United States Patent
Pratap et al.

(10) Patent No.: US 6,579,862 B1
(45) Date of Patent: Jun. 17, 2003

(54) METHOD OF TREATING HYPERLIPIDEMIC AND HYPERGLYCEMIC CONDITIONS IN MAMMALS USING PREGNADIENOLS AND PREGNADIENONES

(75) Inventors: Ram Pratap, Lucknow (IN); Ram Chandra Gupta, Lucknow (IN); Ramesh Chander, Lucknow (IN); Ashok Kumar Khanna, Lucknow (IN); Arvind Kumar Srivastava, Lucknow (IN); Deepak Raina, Lucknow (IN); Satyavan Singh, Lucknow (IN); Savita Srivastava, Lucknow (IN); Anil Kumar Rastogi, Lucknow (IN); Omkar Prasad Asthana, Lucknow (IN); Swarn Nityanand, Lucknow (IN); Nitya Anand, Lucknow (IN); Ashim Ghatak, Lucknow (IN); Narinder Kumar Kapoor, Lucknow (IN); Sukh Dev, Lucknow (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/280,448

(22) Filed: Mar. 30, 1999

(30) Foreign Application Priority Data

Jan. 12, 1999 (IN) .......................................... 67/DEL/99

(51) Int. Cl.$^7$ ...................... A61K 31/58; A61K 31/565; A61K 31/593
(52) U.S. Cl. ...................... 514/169; 514/169; 514/179; 514/180; 514/181; 514/182
(58) Field of Search ................................ 514/169, 179, 514/180, 182, 181

(56) References Cited

FOREIGN PATENT DOCUMENTS

EP 0562849 * 9/1993

OTHER PUBLICATIONS

Townsley et al. (CA 79:111837), abstract of Endocrinology (1973), 93(1), 172081).*

Ahmad–Sorour et al. (CA:95:126605, abstract of Horm. Res. (1980), 13(6), 396–0163).*

Ghaleb et al. (CA 81:72861, abstract of J. Drug Res. (1973), 5(2), 13–21).*

Sutter–Dub et al. (CA 95:91279, abstract of Diabete Metab. (1981), 7(2), 97–104), 1980.*

* cited by examiner

Primary Examiner—Sabiha Qazi
(74) Attorney, Agent, or Firm—Finnegan, Henderson, Farabow, Garrett & Dunner, L.L.P.

(57) ABSTRACT

The invention provides a method of using pregnadienones and pregnadienols represented by the structural formula (I):

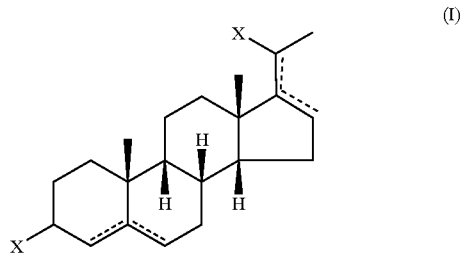

Figure 1A:
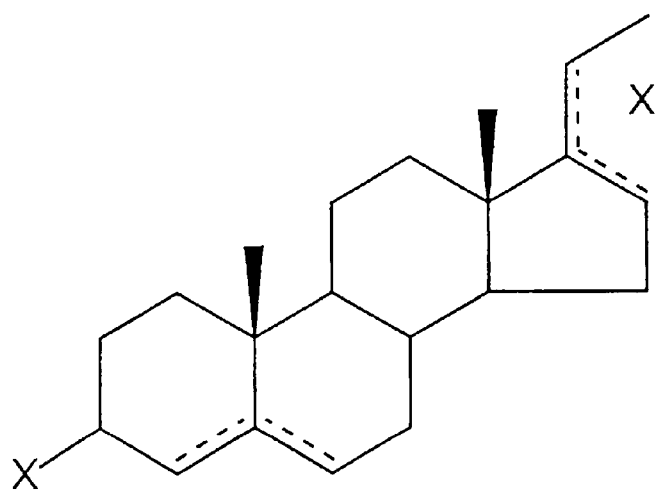

containing at least one olefinic bond in or on their D-ring for the treatment of hyperlipidemic and hyperglycemic conditions in mammals wherein X=OH or O and the olefinic bonds are at 4(5); 5(6); 16(17); or 17(20) or various combinations, and wherein the compounds contain at lest one olefinic bond in or on their D-ring. The method comprises administering an effective amount of said compounds to recipient mammals.

13 Claims, 2 Drawing Sheets

PROGESTERONE

GESTODENE

NORETHISTERONE

3-KETODESOGESTREL

LEVONORGESTREL

GUGULSTERONE

METHOD OF TREATING HYPERLIPIDEMIC AND HYPERGLYCEMIC CONDITIONS IN MAMMALS USING PREGNADIENOLS AND PREGNADIENONES

Pursuant to 35 U.S.C. §119, the present application claims priority of application 67/DEL/99 filed in India on Jan. 12, 1999.

FIELD OF THE INVENTION

This invention relates to the novel use of D-ring unsaturated pregnadienols/pregnadienones represented by general formula I as shown in the accompanying drawings, possessing both pronounced hypolipidemic and hypoglycemic activities and devoid of androgenic and progestational activities. More particularly this invention relates to the novel use of 3β-hydroxy-pregna 5,16-dienone important prototype of this class, represented by the formula (II) as shown in the accompanying drawings, for the treatment of diabetes and pronounced hypolipidemic and hypoglycemic activities.

BACKGROUND

High plasma cholesterol and related lipids are known to be one of the factors that predispose and individual to atherosclerosis and thus to myocardial infraction. Diabetes mellitus, which eventually impairs the function of kidneys, eyes, nervous and vascular systems, is quite often associated with lipid disorders. Both hyperlipidemia and diabetes mellitus require long term management and pose problems in choice of pharmacotherapeutic interventions when these conditions manifest together. Though a number of drugs are known separately to treat these conditions, there are a number of side effects associated with them which limit their long term use.

The most important hypolipidemic drugs available today belong to the strain and fibrate classes [McCarthy, P. A., Med. Res. Rev., 13, 139–59 (1993)] whereas hypoglycemic drugs fall into the category of sulphonylureas, biguanidines and amidines [Wolff, M. E. (Ed), Burger's Medicinal Chemistry Part II, 1045 (1981), John Wiley & Sons, New York]. However, these therapeutic agents are not free of side effects-statins (HMG-CoA reductase inhibitors) the most widely used drugs today which hitherto were thought to be very safe drugs, have exhibited side effects following long term therapy [Carrier, M. et al.; Ann. Thorac. Surg., 57, 353–6 (1994)]. The adverse effects which have become the source of concern, are increases in hepatic transaminases and myopathies [Witztum, J. L., In Goodman & Gilman's The Pharmacological Basis of Therapeutics, eds. Hardman, J. et al., 9$^{th}$ edition, McGraw Hill, New York pp 875–98, Fukami, M. et al; Res. Exp. Med., 193, 263–73 (1993); Appelkvist, E..; et al.; Clin. Invest., 71 (suppl 8), 597–102 (1993), Wills, R. A. et al.; Proc. Natl. Acad. Sci. (US), 87, 8928–30 (1990)] and carcinogenesis specially breast cancer in subjects undergoing treatment with pravastatin [Braunwald, E.; Scrip, 2117, 33 (1996)); Ciaravino, V. et al.; Mutat. Res.; 353, 95–107 (1995)]. The incidence of myopathy associated with rhabdomyolysis and renal failure is increased subsequent to such treatment [East, C. et al.; N. Engl. J. Med., 318, 47–48 (1998); Pierce L. R. et al.; J. Am. Med. Assoc., 265, 71–75 (1990)]. Also, the HMG-CoA inhibitors block mevalonate production which occurs at an early stage in cholesterol synthetic pathway. Meyalonate is a common precursor for all isoprenoids such as ubiquionones (Co-enzyme Q-10), the dolichols, isopentenyl t-RNA etc. Therefore, long term blockade of mevalonate synthesis leads to Q-10 deficiency. Serum Co-enzyme Q-10 is important for cardiac function [Laaksonen, R. et al., Eur. J. Clin. Pharmacol. 46,313–7 (1994); Bargossi, A. M. et al; Int. J. Clin. Lab. Res., 24, 171–6 (1994)]. The commonest side-effects of fibrates and particularly clofibrate therapy are gastrointestinal upsets including nausea, vomiting, diarrhoea, dyspepsia, flatulence and abdominal discomfort [Oliver, M. F. et al.; Br. Heart J., 40, 1069–1118 (1978)]. Elevated creatine phosphokinase concentration during clofibrate therapy may be associated with a syndrome of muscle pain and weakness. Large-scale long-term studies have demonstrated an increased incidence of cholecystitis, gall-stones and sometimes pancreatitis in patients receiving clofibrate and some studies have indicted cardiovascular disorders [The coronary Drug Project Research Group; N. Engl. J. Med., 296, 1185–90 (1977)]. The unexpected finding of an increased mortality rate in patients taking clofibrate in the WHO study produced serious concern over the long-term safety of clofibrate and ultimately led to its withdrawal in many countries [Oliver, M. F. et al; Lancet, ii, 600–604 (1984)].

The adverse effects of biguanidine antidiabetic agents include gastro-intestinal disturbances like diarrhoea and lactic acidosis [Paterson, K. R. et al.; Adverse Drug React Acute Poisoning Rev., 3, 173–82 (1984)]. With sulphonylureas the commonly associated adverse effects are hypoglycemia, gastrointestinal disturbances, hypersensitivity and vascular complications [Paice, B. J. et al., Adverse Drug React. Acute Poisoning, 4, 23–26 (1985)]. As diabetes and hyperlipidemia are quite commonly manifesting together, it would be great clinical benefit if the same compound could have both these activities together because the available drugs are not free of toxic effects and neither data regarding toxic manifestations are available when drugs for two clinical conditions are mixed together.

Two approaches currently being pursued in search of drugs with hypolipidemic and hypoglycemic activities together. The first approach emerged during detailed study of antihypertensive action of adrenergic receptor modulators. The study revealed that $\alpha_1$-adrenergic blockers (particularly Doxazosin and Prazosin) [Lithell, H. O.; J. Hypertens, 15 (Suppl 1), S 39–42 (1997); Poliare, T. et al.; Diabetologia, 31, 415–420 (1988); Anderson, P. E. et al.; Am. J. Hypertens, 9, 323–333 (1996)] and $\beta_3$-adrenergic agonist (BTA-243, BRL-37344, CGP 12177, CL 316243 [Arch, J. R. S. et al.; Med. Res. Rev. 13, 663–729 (1993); Largis, E. E. et al; . Drug Dev. Res., 32, 69–76 (1994)] also affect plasma lipoprotein metabolism and increase insulin sensitivity. As a result such antihypertensive drugs exhibit lipid lowering and hypoglycemic actions together, $\alpha_1$-adrenergic receptor blockers, however have the inherent limitations of causing orthostatic hypotension and syncope [Matyus, P.; Med. Res. Rev., 17(6), 523–35 (1997)]. The essential requirement of $\beta_3$-agonist for antiobesity and antidiabetic actions is the need for high selectivity for $\beta_3$—adrenoceptor. Any substantial $\beta_1$- or $\beta_2$-agonism would likely cause increased heart rate and muscle tremor respectively which are unacceptable in a drug which could be administered on long term basis [Connacher, A. A. et al.; Brit. Med. J., 296, 1271–20 (1988); Mitchell, T. H. et al; Int. J. Obesity., 13(6), 757–66 (1989)]. The second line of approach for dual activity came into light during the study of anti-oxidant property of drugs. There have been many reports describing relationships between peroxidantion and disease such as diabetes mellitus, atherosclerosi and myocardial ischemia in terms of radical oxidation. Troglitazone, an antioxidant drug has been developed as an oral hypoglycemic agent which enhances the action of insulin in peripheral tissues and liver besides its hypolipidemic effects. However, troglitazone is also not free of major side effect causing liver damage. The drug, troglitazone, has been implicated in 35 cases of liver disease leading to one transplant and one death [Warner-Lambert; Chem. & Ind., No.22, 897 (1997)]. Thus to the best of our knowledge no class of compound is yet available which has both effects together as the main action and have fair safety margin.

We, in early eighties started our work for search of such compounds which have effect on endogenous transportation of lipids and glucose rather than interfering with exogenous transportation. Our research was mainly based on secondary metabolic actions of progesterone.

Progesterone, apart from its clinical hormonal action on the reproductive system, is known to modulate lipid, carbohydrate, insulin and protein metabolism. The rise in the level of progesterone in the first trimester of pregnancy causes hyperphagia, pancreatic islet hypertrophy, hyperinsulinemia and body fat and glycogen deposition, when the metabolic demands of the fetus are very low. However, in the latter half of pregnancy, although the progesterone levels are still high, the carbohydrate, lipid and protein reservoirs shift into circulation to meet the needs of the growing fetus [Kalhoff, R. K.; Am. J. Obstet. Gynecol., 142, 735–38 (1982)].

Progesterone thus, having actions both on the reproductive and the metabolic systems, seemed to offer the possibility of dissociating these two biological activities by structural modifications. The experience of the development of second generation progestins supported this contention. The first generation progestins such as levonorgestrel exhibited undesirable pharmacologic effects like alteration in carbohydrate and lipoprotein metabolism, weight gain and hypertension, which was shown to be related to their intrinsic androgenic/anabolic activity and ability to bind with androgen receptors. The androgenic affinity has been attributed to C-17 hydroxy functionality which makes these molecules resemble androgens. In recently discovered second generation progestins such as gestodene and 3-keto-desogestrel, an additional olefinic bond either in C- or D-ring brought a dramatic decrease in their affinity to androgen receptors (Table 1). As a result these compounds have a very high order of progestational effect with practically no androgenic activity and did not cause hyperlipidemia [London, R. S.; Obstetrical & Gynecological Survey, 47, 777–81 (1992)].

TABLE 1

Relative Binding Affinity of Contraceptive Progestins for Progesterone and Androgen receptors

|  | Progestin Receptor Binding Affinity | Androgen Receptor Binding Affinity | Selectivity Index* (A/P ratio) |
| --- | --- | --- | --- |
| Progesterone | 1.00 | 0.005 | 93 |
| Levonorgestrel | 5.41 | 0.220 | 11 |
| 3-Keto-desogestrel | 8.6 | 0.120 | 33 |
| Gestodene | 9.21 | 0.154 | 28 |

*The higher the selectivity index the greater the separation between the dose needed to achieve the desired progestational effect and the dose associated with the undesired andiogenic effect [Collins, D.C.; Am. J. Obstet. Gynecol. 170, 1508–13 (1994)].

OBJECTS OF THE INVENTION

It is an object of the invention to explore the possibility of designing pregnadienones which while preserving the ability to modulate lipid and carbohydrate metabolism would not have any progestational effect. It would be pertinent to point that earlier, the applicants had isolated a D-ring modified pregnenolone, named Gugulsterone represented by formula (9) as shown in Table 2, from guggul resin obtained from *Commiphora mukul*, which had potent hypolipidemic effect without any progestational effect [Arya, V. P.; Drugs Fut. 13, 618 (1998)].

It is another object of the invention to explore the possibility of dissociating the hypolipidemic and insulin sensitizing activities of progesterone from its hormonal actions. Accordingly, the applicants focussed their attention to prepare and investigate analogues/prototypes with additional substituents in ring-D of pregnadienones.

BRIEF DESCRIPTION OF THE ACCOMPANYING DRAWINGS

Figure 1B:
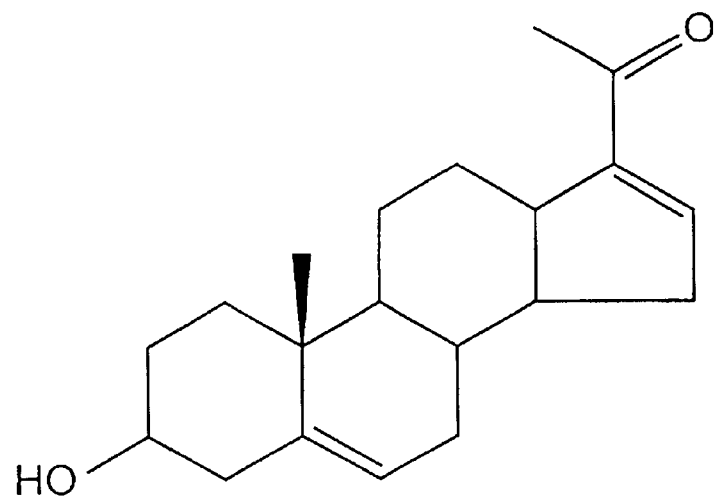
Figure 2A:
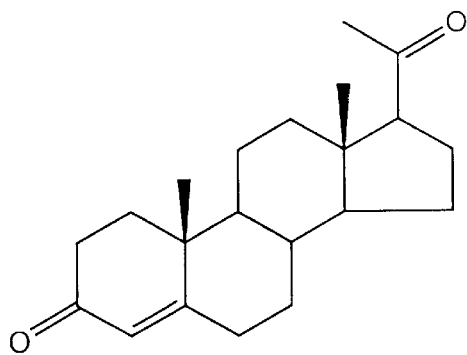
Figure 2B:
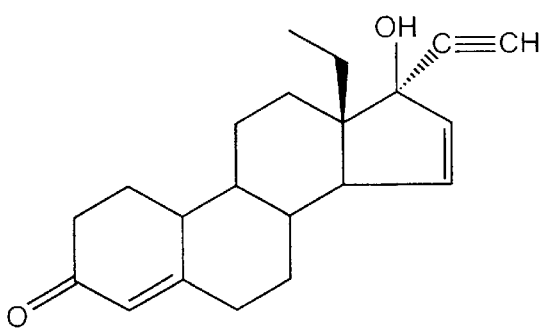
Figure 2C:
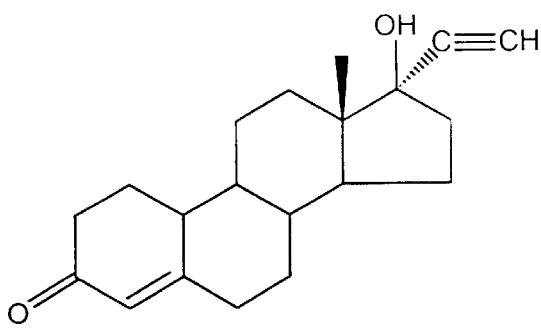
Figure 2D:
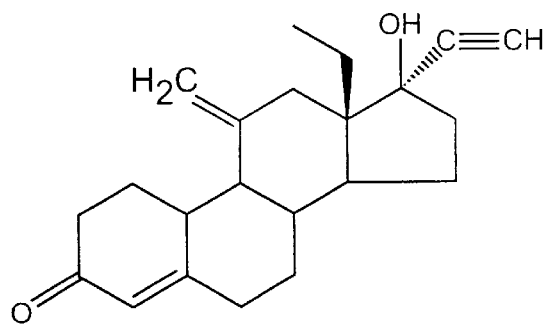
Figure 2E:
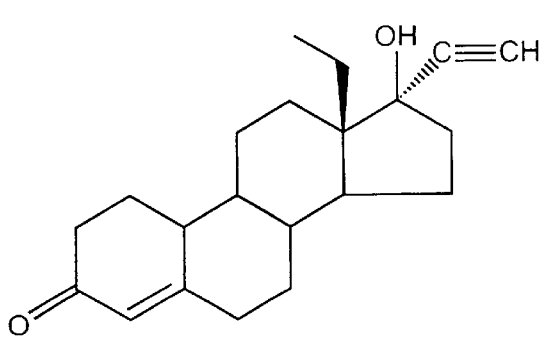
Figure 2F:
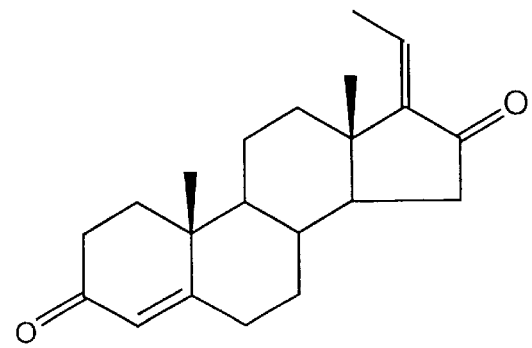

FIG. 1A represents the structural formula of compounds belonging to the class of pregnadienones and pregnadienols and FIG. 1B represents the structural formula of 3β-hydroxypregna-5,16-dien-20-one FIGS. 2A–2F represent the structural formula of hormones.

SUMMARY OF THE INVENTION

In accordance with the above objects, the applicant's present invention relates to a method of using D-ring unsaturated pregnadienones represented by structural formula I which causes significant fall of serum cholesterol, triglycerides, LDL-cholesterol and glucose with mild increase in HDL-cholesterol, said method comprising administration of effective amounts of said compounds of formula (I) to mammals. The compounds possess fair safety margin having antioxidant and cardio protection activities.

The invention also provides a method of treatment of hyperlipidemic and hyperglycemic conditions which comprise administration to a recipient a therapeutic composition comprising a pharmaceutically effective amount of compound D-ring unsaturated pregnadienones represented by the general formula I as shown hereinbelow and in the accompanying drawings:

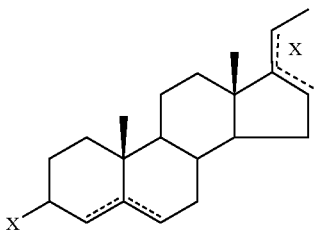

I

Wherein X=OH or O or combination thereof and positioning of olefinic bonds are at 4(5); 5(6); 16(17); 17(20) or various combinations

DETAILED DESCRIPTION OF THE INVENTION

The present invention concerns methods for lowering serum cholesterol, triglycerides and glucose levels in subjects with obesity and diabetic conditions or prophylactically holding in check the symptoms of such a disease state.

In particular, the applicants, during the study, have observed that the pregnadienone, 3β-hydroxypregna-5,16-dien-20-one represented by the structural formula (II) shown hereinbelow and in the accompanying drawings is useful for the treatment of hyperlipidemic and hyperglycemic conditions.

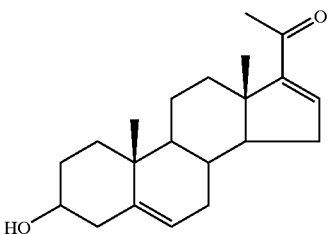

II

Accordingly, the invention provides a method of using compounds represented by the structural formula (I) as shown in the accompanying drawings, containing at least one olefinic bond in or on their D-ring for the treatment of hyperlipidemic and hyperglycemic conditions in mammals, said method comprising administering an effective amount of the compounds to recipient mammals.

In one embodiment, the compounds of formula (I) are administered in the form of tablets, capsules or injectibles.

In another embodiment, the compounds of formula (I) are characterised as pregnadienones and pregnadienols.

In yet another embodiment, the most preferred compound belonging to the family of preganienones and pregnadienols represented by formula (I) is 3β-hydroxy-pregna-5,16-dien-20-one, which is represented by the structural formula (II) as shown in the accompanying drawings.

In a further embodiment, the compounds of formula (I) are optionally administered to the recipient mammal as an admixture with conventional anti-platelet, anti artheroscloerotic, hypolipoproteinic and antidiabetic drugs.

In still another embodiment, the compounds of formula (I) are essentially free of side effects associated with conventional hypolipidemic and hypoglycemic drugs.

In an embodiment, the compounds of formula (I) exhibit cardioprotective, anti-diabetic, anti-artherosclerotic and anti-oxidant properties.

Further, the invention provides a method of treatment of hyperlipidemic and hyperglycemic conditions in mammals, which comprises administration to a recepient, a therapeutic composition comprising an effective amount of the compound of formula (I) with conventional carriers.

In an embodiment, the recipient mammals are selected from the group comprising rats, human beings, rhesus monkeys and rabbits.

In another embodiment, the conventional carriers are selected from anti-platelet, anti-artherosclerotic, hypolipoproteinic and anti-diabetic drugs.

In yet another embodiment, the said compounds of formula (I) essentially contain an olefinic bond in or on their D-ring.

In a further embodiment, the compounds of formula (I) are essentially free of androgenic, progestinal and side effects.

In still another embodiment, the therapeutic composition is administered in the form of tablets, capsules and injectibles.

In another embodiment, the said preganadienones and preganadienols exhibit cardio protective, antidiabetic, anti-altheroselerotic and antioxidant properties.

In yet another embodiment, the said preganadienones and pregnadienols of formula I essentially contain olefinic bond in one of the D-rings.

METHODS OF SYNTHESIS/PRODUCTION

The methods of synthesis are essentially known in the literature, can be obtained from diosgenin by chemical degradation [G. Rosenleranz "History of Steroids", Steroids, 57, 409 (1992)]. Although, it was later isolated from Veratrum Grandiflorum [Kanko, K. et al; Phytochemistry, 12 1509 (1973)] but yield is too low to be of any practical value. Oppenauer oxidation of 2 with aluminium-isopropoxide and cyclohexanone in toluene produces 4,16-dienpregna-3,20-dione [16-dehydroprogesterone. (3)]. The C-16(17) olefinic bond in 1 is selectively reduced with Pd-C in diethylether at very low hydrogen gas pressure. The resultant product 4 on basic hydrolysis furnishes 5. The procedure of Benn and Dodson [J. Org. Chem. 29, 1142 (1964)] was followed for the preparation of Guglsterone (9). The reduction of 16-DPA (1) with lithium aluminum hydride produces diol 6 which after Sigmatropic rearrangement in presence of p-toluenesulphonic acid, acetic acid and acetic anhydrode produces the diacetate 7. Basic hydrolysis of the diacetate 7 followed by Oppenauer oxidation furnishes an 80:20 mixture of E&Z -Gugulsterone (9).

5. BIOLOGICAL ACTIVITY 5.1 Hypolipidemic Activity

The primary hypolipidemic effect of these compounds were established in triton induced hyperlipidemia in Charles Foster rats. The compounds which exhibited significant lipid lowering effect in this model were then evaluated for their hypolipidemic effect in normal, and diet induced hyperlipidemic rats, rabbits and rhesus monkeys.

5.1.1. Hypolipidemic Activity in Triton Treated Rats

The cholesterol lowering effect of some representative compounds of pregnadienols and pregrenadienones as compared to clofibrate and gugulsterone in triton treated Charles Foster rats is described in Table-2

TABLE 2
Cholesterol lowering effect of pregnane compounds as compared to Clofibrate in Triton treated rats
| Compd. No. | Compound | Structure | Dose (i.p.) mg/kg | % Change S. Chol. |
|---|---|---|---|---|
| 1 | 3β-Acetoxypregna-5,16-dien-20-one (16-DPA) | 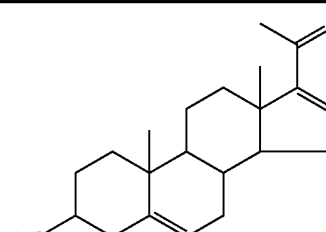 | 50 | −43 |
| 2 | 3β-Hydroxypregna-5,16-dien-20-one | 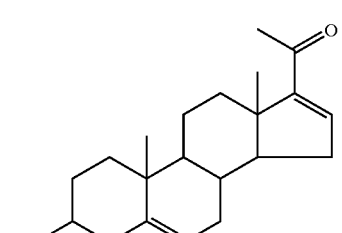 | 50 | −46 |
| 3 | 4,16-Dienpregna-3,20-dione | 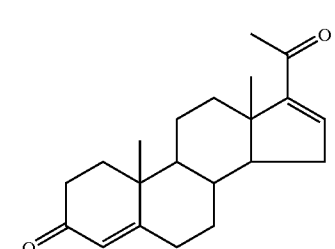 | 50 | −13 |
| 4 | 3β-Acetoxypregna-5-en-20-one | 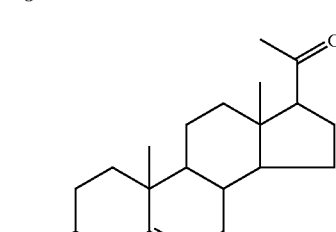 | 100 | −12 |
| 5 | 3β-Hydroxypregna-5-en-20-one | 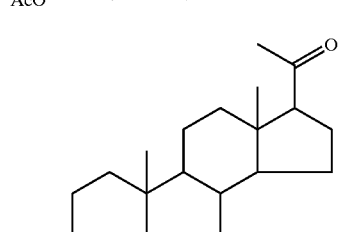 | 100 | −09 |
| 6 | 5,16-Dien-pregnane-3,20-diol | 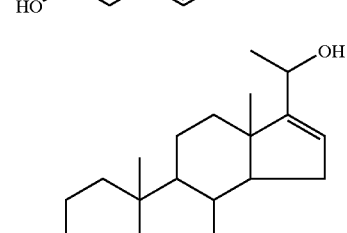 | 50 | −10 |

TABLE 2-continued

Cholesterol lowering effect of pregnane compounds as compared to Clofibrate in Triton treated rats

| Compd. No. | Compound | Structure | Dose (i.p.) mg/kg | % Change S. Chol. |
|---|---|---|---|---|
| 7 | 5,17(20)-Dienpregna-3,16-diol-diacetate | 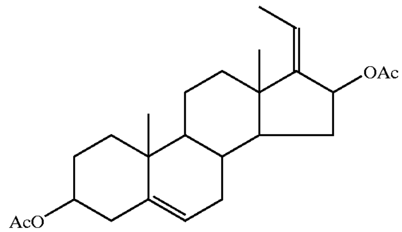 | 50 | −33 |
| 8 | 5,17(20)-Dienpregna-3,16-diol | 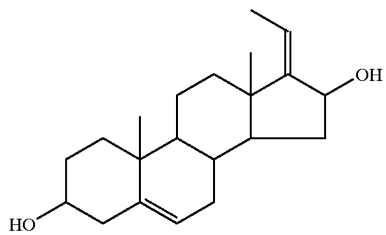 | 50 | −31 |
| 9 | Gugulsterone | 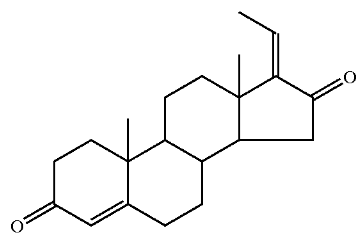 | 50 | −44 |
| 10 | Clofibrate | | 200 | −15 |

The results showed that of the compounds tested, the highest effect was exhibited by 16-DPA (1) and its 3-desacetyl analog 2 comparable to gugulsterone (9), and that the removal of double bond in ring D of 1 of 2 almost abolished the effect.

5.1.2 Hypolipidemic Activity of 3β-Hydroxypregna-5,16-dien-20-one (2) in Normal Rats In normal rats, 3β-hydroxypregna-5,16-dien-20-one (2), at 50 mg/kg produced a significant lowering of serum cholesterol and triglycerides as described in Table-3 below. The animals did not develop any tolerance to the compound even after administering for 30 days.

TABLE 3

Hypolipidemic activity of 3β-Hydroxypregna-5,16-dien-20-one (2) in normal rats

| Treatment | Serum Cholesterol (mg %) | | | Serum Triglycrides | % Fall compared |
|---|---|---|---|---|---|
| | 0 Days | 30 Days | % Fall | (mg %) 30 Days | to control |
| 2 (50 mg/kg) (8) | 71.5 ± 1.8 | 43.2 ± 2.9 | 40 | 42.0 ± 2.8 | 35 |
| Clofibrate (50 mg/kg) (6) | 82.3 ± 3.3 | 53.2 ± 2.0 | 36 | 47.3 ± 3.2 | 28 |
| Normal saline (control) (6) | 83.3 ± 3.1 | 80.1 ± 1.4 | — | 65.2 ± 2.9 | — |

Mean values ± SD.
Figure in parenthesis represent number of animals.

5.1.3 Hypolipidemic Activity in Diet Induced Hyperlipidemic Rats

Twenty three normal male rats average weight 110–120 g were taken for study and were divided into four groups Group I: animals received special diet and 3β-hydroxypregna-5,16-dien-20-one (2) 50 mg/kg p.o. in 1% gum acacia. Group II: animals received 3β-hydroxypregna-5,16-dien-20-one (2), 100 mg/kg p.o. in 1% gum acacia and special diet. Group III:animals received special fat diet and 1% gum acacia and served as control. Group IV: animals were fed with stock diet and served as normal control. All animals were sacrificed at the end of 36 days. Blood was drawn from the tail at 10 days and from the aorta at the time of sacrifice for estimation of serum cholesterol, triglycerides and HDL-cholesterol. LDL-cholesterol was calculated as described. [Roschlau, P. In: Methods of Enzymatic Analysis 4th ed., H. U. Bergmeyer, Ed (Academic Press, New York) 1975 p 1890; Wahlefiled, W. A. In:Methods of Enzymatic Analysis, 4th ed.; H. U. Bergmeyer, Ed.(Academic Press, New York) 1974 p 1831.]

Results

Animals treated with 3β-hydroxypregna-5,16-dien-20-one (2), at 50 and 100 mg/kg showed a significant lowering in serum cholesterol by 31 and 59%, triglycerides by 55 and 62%, LDL-cholesterol by 27 and 74% respectively (Table 4 & 5).

TABLE 4

Effect of 3β-Hydroxypregna-5,16-dien-20-one (2) on serum cholesterol and triglycerides in hyperlipidemic rats

| Treatment | Serum Cholesterol (mg %) Days | | | Serum Triglycerides (mg %) | |
|---|---|---|---|---|---|
| | 0 | 10 | 36 | 0 | 36 |
| I 2 (50 mg/kg) + HFD | 69.1 ± 9.9 (7) | 212.4 ± 23.8 (7) | 165 ± 26.7 (7) | 48.8 ± 7.0 (6) | 61.5 ± 10.5 (6) |
| % Decrease (Compound to group III) | | 16 | 31 | | 55 |
| II 2 (100 mg/kg) + HFD | 60.8 ± 10.3 (6) | 145.5 ± 10.6 (6) | 106.4 ± 4.6 (5) | 50 ± 7.1 (5) | 53.0 ± 7.5 (5) |
| % Decrease (Compound to group III) | | 48 | 59 | | 62 |
| III HFD | 73.2 ± 5.8 (5) | 325 ± 29.8 (5) | 293.2 ± 16.6 (5) | 48.75 ± 5.1 (4) | 137.5 ± 8.5 (4) |
| IV Normal Diet | | 72 ± 7.1 (5) | | | 48.2 ± 4.3 (5) |

HFD = High for diet,
Values are Mean ± SD.
Figures in parenthesis are number of animals

TABLE 5

Effect of 3β-Hydroxypregna-5,16-dien-20-one(2) on HDL and LDL-cholesterol in hyperlipidemic rats

| Treatment | HDL-Cholesterol (mg %) | | LDL-Cholesterol (mg %) | |
|---|---|---|---|---|
| | Day 0 | Day 36 | Day 0 | Day 36 |
| I HFD | 37.25 ± 5.0 (4) | 39.75 ± 2.8 (4) | 27.5 ± 6.3 (4) | 189.25 ± 18.0 (4) |
| II 2 (50 mg/kg) + HFD | 34.8 ± 5.8 (7) | 37.57 ± 2.8 (7) | 24.5 ± 14.2 (7) | 123.87 ± 14.0 (6) |
| % Change | | 181 | | 271 |
| III 2 (100 mg/kg) + HFD | 43.4 ± 8.3 (5) | 47.2 ± 3.7 (5) | 10.02 ± 8.5 (5) | 48.64 ± 5.1 (5) |
| % Change | | 161 | | 741 |

HFD = High fat diet.
Values are Mean ± SD.
Figures in parenthesis are number of animals

5.1.4 Hypolipidemic Activity in Hyperlipidemic Rabbits

Effects of 3β-hydroxypregna-5,16-dien-20-one (2) was studied on hypercholesterolemic albino rabbits. Twelve male albino rabbits (approx. 1.5–2 kg) on a stock diet were made hyperlipidemic by feeding daily cholesterol 0.5 g/kg in 2 ml of groundnut oil for 45 days and then blood was drawn from the marginal vein in the ear of rabbits for serum cholesterol and triglycerides estimation.

Two controlled experiments were carried out for a period of three months. In one set of experiments, the control group received 0.5 g/kg of cholesterol for 90 days and 3β-hydroxypregna-5,16-dien-20-one (2) in dose of 100 mg/kg and 50 mg/kg while in the control group (given only cholesterol) a massive rise of sterum cholesterol and triglycerides were seen after 90 days, the addition of 3β-hydroxypregna-5,16-dien-20-one(2) at 50 and 100 mg/kg doses kept the rise well under control. The percentage decrease at 100 mg dose was 28% at 30 days to 52% at 90 days for cholesterol and 45 to 81% for triglycerides. In the 50 mg/kg dose group the decrease percentage ranged from 40% at 30 days at 50% at 90 days for cholesterol and 45% at 30 days to 75% at 90 days for triglyceride (Table-6)

TABLE 6

Effect of 3β-Hydroxypregna-5,16-dien-20-one (2) in hyperlipidemic male-albino rabbits

| Treatment | S. Cholesterol (mg %) Days | | | S. Triglycerides (mg %) Days | | |
|---|---|---|---|---|---|---|
| | 30 | 60 | 90 | 30 | 60 | 90 |
| Expt. I.A<br>Control + cholesterol<br>(0.5 g/kg) | 296.3 | 435.5 | 1337.5 | 69.0 | 150.0 | 161.0 |
| Expt. I.B<br>(2 (100 mg/kg) +<br>cholesterol (0.5 g/kg) | 213.3 | 309.3 | 633.7 | 79.0 | 54.0 | 44.2 |
| % Decrease | 28 | 42 | 53 | 46 | 64 | 81 |
| Expt. II.A<br>Control + cholesterol<br>(0.5 g/kg) | 317.8 | 531.8 | 1334.6 | 145.0 | 185.8 | 232.0 |
| Expt. II.B<br>2 (50 mg/kg) +<br>cholesterol (0.5 g/kg) | 190.5 | 305.5 | 660.3 | 79.5 | 67.0 | 56.5 |
| % Decrease | 40 | 43 | 51 | 45 | 64 | 76 |

TABLE 7

Hypolipidemic effect in hyperlipidemic rabbits (120 days experiment)

| Parameters | Stock diet + Normal saline | HFD | HFD + Guglip + 2 (100 mg/kg) | HFD + 2 (100 mg/kg) |
|---|---|---|---|---|
| Serum Cholesterol (mg/dl) | 56.3 ± 3.1 | 1367.0 ± 203 | 258.6 ± 28.2 | 350.0 ± 28.1 |
| % Decrease (Compared with HFD) | | | 81 | 74 |
| Serum Triglycerides | 50.0 ± 2.1 | 188.0 ± 10.2 | 66.2 ± 4.1 | 74.2 ± 10.3 |
| % Decrease (Compared with HFD) | | | 65 | 61 |

5.1.5 Hypolipidemic Activity in Rhesus Monkeys

In Rhesus monkeys: 3β- Hydroxypregna-5,16-dien-20-one (2) was administered orally daily for 90 days in doses of 62.5, 125 or 650 mg/kg to different group of animals. Significant decrease in serum cholesterol was observed (45–52%). At 90 days, percentage decrease in triglycerides varied from 14 to 36%. Compound 2 caused a marked decrease in low density lipoprotein (75–90%) whereas changes in HDL-cholesterol were not significant (Table-8 & 9)

TABLE 8

Effect of 3β-Hydroxypregna-5,16-dien-20-one (2) in Rhesus monkeys

| Treatment | S. Cholesterol Days | | | S. Triglycerides Days | | |
|---|---|---|---|---|---|---|
| | 0 | 90 | % Fall | 0 | 60 | % Fall |
| Expt. I<br>Control + 1% gum acacia | 119.8 ± 16.6 | 90.5 ± 9.0 | 26 | 82.0 ± 2.5 | 62.0 ± 1.0 | 24 |
| Expt. II 2 (62.5 mg/kg) | 156.8 ± 23.0 | 83.3 ± 8.5 | 47 | 77.5 ± 7.0 | 66.3 ± 6.9 | 14 |
| Expt. III 2 (125 mg/kg) | 133.3 ± 8.5 | 65.8 ± 2.2 | 50 | 69.8 ± 9.9 | 60.0 ± 2.9 | 13 |
| Expt. IV 2 (650 mg/kg) | 132.8 ± 6.4 | 63.3 ± 2.3 | 53 | 90.5 ± 3.9 | 58.5 ± 3.8 | 36 |

Mean ± SD values mg/dl.
Each set of experiment involved 4 monkeys

TABLE 9

Effect of β-Hydroxypregna-5,16-dien-20-one (2) on HDL- and LDL-cholesterol in Rhesus monkeys

| Treatment | HDL-Cholesterol Days | | | LDL-Cholesterol | | |
|---|---|---|---|---|---|---|
| | 0 | 90 | % Change | 0 | 90 | % Full |
| Expt. I<br>Control + 1% gum acacia | 45.5 ± 7.4 | 43.0 ± 0.5 | −6 | 57.9 ± 16.2 | 35.0 ± 8.8 | 39 |
| Expt. II 2 (62.5 mg/kg) | 50.0 ± 4.5 | 45. ± 2.5 | −8 | 91.8 ± 27.0 | 24.3 ± 8.0 | 75 |
| Expt. III 2 (125 mg/kg) | 46.3 ± 2.0 | 50.8 ± 0.5 | +10 | 63.5 ± 7.4 | 4.6 ± 0.9 | 90 |
| Expt. IV 2 (650 mg/kg) | 39.3 ± 1.3 | 41.8 ± 0.9 | +6 | 72.7 ± 8.4 | 13.1 ± 0.7 | 82 |

Mean ± SD values mg/dl.
Each set of experiment involved 4 monkeys.

5.2 Hypoglycemic Activity

The compounds were tested for their hypoglycemic effects in normal, glucose loaded and streptozotocin induced diabetic rats. The experimental details of the testing of one such compound 3β-hydroxypregna-5,16-dien-20-one (2) is described below which possessed marked hypoglycemic effect in two models. (Tables 10 and 11)

5.2.1 Hypoglycemic Activity in Glucose Loaded Rats

The experiments were carried out with albino rats (Charles Foster strain) of either sex weighing 150–160 g. They were fed on laboratory diet prepared by M/s Lipton India Ltd. and maintained under 12 hr. light/dark cycle at 25±2° C.

The animals were divided into eight groups, each of six rats; group I was given 1% gum acacia (0.1 ml/100 g body weight) intragastrically (p.o.) and the group II were given 3β-hyrdoxypregna-5,16-dien-20-one(2) in 1% gum acacia, Animals of groups III were given the standard antidiabetic drug, tolbutamide in the similar fashion 2.0 g/kg glucose was given p.o. to all the rats along with the vehicle/Compound/Standard antidiabetic drug. Blood samples were taken from retroorbital plexus at periodic intervals. Glucose levels in the blood samples were measured by glucose oxidase method [Bergmeyer and Benut, 1963 cited in "Methods of Enzymatic Analysis" ed. H. Bergmeyer, Verlag Chemie, GmBH, Winheim, Beroster, pp123, Academic press, New York].

cell membranes and lipoproteins are oxidized and resulting active specie modify macrophages and bystander cells monocytes which then move to subendothelial space, energy cholesteryl esters and are transformed into what are known as foam cells. Group of these foam cells form atherosclerotic plaques in the intima. The antioxidant potential of compound 2 was evaluated against metal induced oxidation of LDL as well as generation of hydroxy (OH) radical.

In vivo experiment with cholesterol fed animals marked formation of lipid peroxides in serum lipoproteins. Simultaneous treatment with compound 2 caused significant reversal of the lipid peroxide levels in serum VLDL, LDL and liver in cholesterol fed animals. However gemfibrozil failed to protect the phenomenon of lipid peroxidation (Table 12).

TABLE 10

Effect of 3β-Hydroxypregna-5,16-dien-20-one (2) and standard antidiabetic drug on post-prandial blood glucose level after challenge with glucose

| Group | Blood Glucose Level (mg/dl) | | | | | Maximum Blood Glucose Change (%) |
|---|---|---|---|---|---|---|
| | 0 min | 30 min | 60 min | 90 min | 120 min | |
| Control | 40.35 ± 2.9 | 102.3 ± 6.11 | 68.91 ± 1.95 | 66.48 ± 2.12 | 50.61 ± 1.27 | |
| Compound 2 (100 mg/kg) + Glucose | 42.43 ± 1.64 | 76.15 ± 6.07 (48) | 56.06 ± 4.65 (55) | 55.06 ± 2.61 (54) | 49.59 ± 1.66 (34) | −18.7 |
| Tolbutamide (100 mg/kg) + Glucose | 38.15 ± 2.02 | 76.31 ± 6.29 (35) | 27.26 ± 3.1 (100) | 24.64 ± 1.92 (100) | 23.07 ± 3.11 (100) | −41.7 |

Figure in parenthesis indicates % inhibition compared to control
Mean ± SD values mg/dl.
Each set of experiment involved 6 rats.

5.2.2 Hypoglycemic Activity in Streptozotocin Induced Hyperglycemic Rats

Hyperglycemia in rats was produced by streptozotocin treatment. The animals showing blood glucose levels between 250–350 mg/dl were selected. Blood samples were collected after treatment at intervals and blood glucose levels were estimated immediately. The results showed lowering in blood glucose levels within 1 hr and the maximum fall was observed at 12 hours.

Human serum LDL was oxidized with $Cu^{12}$ in different concentrations of test compound in 0.05 mole PBS, pH 7.4 for 16 hr at 37° C. Thiobarbituric acid reactive lipid peroxides are measured by standard procedure. Compound 2 and α-tocopherol inhibit the generation of LDL lipid peroxide in concentration dependent manner. However the gemfibrozil at tested concentrations did not inhibit the oxidative modification (Table 13). $Cu^{12}$ induced oxidation in LDL lipids are mainly due to the free OH radical during incubation. There-

TABLE 11

Effect of 3β-Hydroxypregna-5,16-dien-20-one (2) and Tolbutamide on blood glucose level of streptozotocin induced diabetic rats.

| Treatment | Blood glucose level mg/dl | | | | | | | | | |
|---|---|---|---|---|---|---|---|---|---|---|
| | 0 hr | 1 hr | 2 hr | 3 hr | 4 hr | 5 hr | 6 hr | 7 hr | 8 hr | 24 hr |
| I Streptozotocin (50 mg/kg i.p.) | 301 ± 7 | 314 ± 11 | 318 ± 12 | 328 ± 10 | 328 ± 15 | 333 ± 21 | 347 ± 19 | 355 ± 24 | 340 ± 22 | 349 ± 12 |
| II Streptozotocin (50 mg/kg p.o)$^{+2}$ (100 mg/kg p.o.) | 274 ± 9 | 243* ± 10 (11.3) | 231* ± 14 (15.6) | 203** ± 20 (25.9) | 183*** ± 14 (33.2) | 157*** ± 21 (42.7) | 133*** ± 16 (51.4) | 102*** ± 9 (62.7) | 91*** ± 8 (66.7) | 128*** ± 18 (52.2) |
| IV Streptozotocin (50 mg/kg i.p. + Tolbutamide (100 mg/kg p.o.) | 292 ± 10 | 218** ± 14 (25.3) | 207** ± 17 (29.1) | 202** ± 19 (30.8) | 195** ± 23 (33.2) | 183** ± 23 (37.3) | 174*** ± 23 (40.4) | 192** ± 29 (34.2) | 242* ± 18 (17.1) | 332 ± 26 |

Mean ± SD values mg/dl.,
Parenthesis shows % lowering from zero hour value.
*P < 0.05,
**P < 0.01,
***P < 0.001

5.3 Antioxidant Activity

The free radical oxidative stress has been implicated in the pathogenesis of a variety of human disease conditions including atherosclerosis. Polyunsaturated fatty acids within fore the effect tested for generation of OH radical in vitro in nonenzymatic system of $Fe^{12}$, sodium ascorbaic, hydrogen-peroxide and deoxyribose oxidative attack of oxy radical on deoxyribose caused fragmentation and formation of dialdehyde which are spectrophotometrically measured after their reaction with thiobarbituric acid. As observed in case of oxidation of LDL by metal ion, the compound 2 inhibits the generation of OH radical in concentration dependent manner. However, the activity of 2 is of low order to that of mannitol, a selective inhibitor of OH radical (Table 14)

TABLE 12

Effect of 3β-Hydroxypregna-5,16-dien-20-one (2) on lipid peroxidation in cholesterol fed hyperlipidemic rats.

| Serum/Tissue | Control | Cholesterol Fed | Cholesterol + Drug (25 mg/kg) | |
|---|---|---|---|---|
| | | | Compound 2 | Gemfibrozil |
| Serum a | 675 ± 82 | 1228 ± 130 (+82) | 931.5 ± 51 (−24) | 1161 ± 74 (−5) |
| VLDL a | 237 ± 25 | 379 ± 20 (+60) | 310 ± 15 (−18) | 346 ± 10 (−9) |
| LDL a | 351 ± 17 | 604 ± 24 (+72) | 421 ± 20 (−30) | 568 ± 62 (−6) |
| HDL a | 123 ± 13 | 138 ± 17 (+12) | 125 ± 10 (−9) | 134 ± 13 (−3) |
| Liver b | 74 ± 8 | 274 ± 28 (+57) | 212 ± 16 (−23) | 253 ± 26 (−8) |

Values are mean ± SD of 6 rats; a = n mol MDA/dl, b = n mol MDA/g. Values in the parenthesis below drug treated groups are % reversal as compared with cholesterol fed rats.

TABLE 13

Effect of 3β-Hydroxy-pregna-5,16-dien-20-one (2), gemfibrozil and α-Tocopherol on low density lipoprotein oxidation.

| Concentration (μmol/ml) | | Compound 2 MDA | Gemfibrozil MDA | α-Tocopherol | | |
|---|---|---|---|---|---|---|
| | | | | Conc. (μmol/ml) | | MDA |
| None | | 56.5 ± 3 | 52.0 ± 5.4 | None | | 47.4 ± 3.8 |
| 2.5 | Ref. | 56.0 ± 5.8 | 52.8 ± 5.7 | 0.25 | Ref. | 47.4 ± 4.5 |
| | Exp. | 41.4 ± 1.7 (26) | 53.0 ± 6.0 (—) | | Exp. | 44.7 ± 4.5 (3) |
| 5.0 | Ref. | 56.4 ± 5.6 | 50.7 ± 6.1 | 0.5 | Ref. | 47.3 ± 4.5 |
| | Exp. | 28.7 ± 4.0 (49) | 48.8 ± 6.7 (5) | | Exp. | 41.6 ± 4.0 (13) |
| 10.0 | Ref. | 40.6 ± 3.7 | 49.4 ± 5.2 | 1.0 | Ref. | 47.4 ± 3.9 |
| | Exp. | 10.6 ± 0.5 (74) | 43.8 ± 4.9 | | Exp. | 35.0 ± 3.8 |
| 20 | Ref. | 37.2 ± 0.8 | 49.0 ± 2.9 | 2.0 | Ref. | 47.4 ± 4.4 |
| | Exp. | 4.0 ± 0.5 (89) | 41.4 ± 5.0 (16) | | Exp. | 24.3 ± 2.0 (51) |

Values expressed as n mol MDA/mg protein are mean ±SD of four separate experiments. Values in the parenthesis are % inhibition.

TABLE 14

Inhibition of Hydroxy (OH) radical formation in nonenzymatic system.

| Concentration (μmol/ml) | Compound 2 (nmol MDA/hr) | Gemfibrozil (nmol MDA/hr) | α-Tocopherol | |
|---|---|---|---|---|
| | | | Conc. (μmol/ml) | (nmol MDA/hr) |
| None | 90.4 ± 3.8 | 83.4 ± 7.5 | None | 78.2 ± 7.0 |
| 5 | 65.0 ± 5.4 (28) | 79.9 ± 6.8 (4) | 1 | 60.4 ± 7.0 (23) |
| 10 | 52.8 ± 4.2 (42) | 78.5 ± 8.0 (5) | 2 | 45.2 ± 3.3 (42) |
| 20 | 23.3 ± 1.8 (74) | 76.8 ± 7.4 (8) | 3 | 32.4 ± 3.5 (59) |
| 30 | 11.7 ± 1.3 (87) | 76.4 ± 3.8 (8) | 4 | 27.1 ± 2.8 (65) |
| 40 | 10.4 ± 2.0 (88) | 74.3 ± 6.3 (11) | 5 | 20.9 ± 2.0 (73) |
| 50 | 9.9 ± 0.8 (90) | 72.4 ± 8.0 (13) | — | — |

Values are mean + SD of four separate observations.
Values in the parenthesis are % inhibition.

5.4 Cardiac Protection

The underlying cause of mycardial infarction is believed to be the progressive deposition of lipids and fibrotic material into the arterial wall. These pregnadienols and pregnadienous also provided cardiac protection as assessed in isoproterneol induced myocardial necrosis in rat model, which produces myocardial infarction due to an increased blood pressure and heart rate. The protection was comparable with that of gemfibrozil as described in Table 15.

TABLE 15

Effect of 3β-Hydroxypregna-5,16-dien-20-one (2) on serum and tissue parameters of heart necrosis at 25 mg/kg (p.o.) in rats.

| Parameters | Isoproterneol (85 mg/kg, p.o.) % Change | Isoproterneol + Drug (25 mg/kg) % Protection | |
|---|---|---|---|
| | | Gemfibrozil | Compound 2 |
| Serum | | | |
| CPK | 109.91 | 33.9 | 35.7 |
| GOT | 41.61 | 24.9 | 27.0 |
| GPT | 85.01 | 33.4 | 22.7 |

TABLE 15-continued

Effect of 3β-Hydroxypregna-5,16-dien-20-one (2) on serum and tissue parameters of heart necrosis at 25 mg/kg (p.o.) in rats.

| Parameters | Isoproterneol (85 mg/kg, p.o.) % Change | Isoproterneol + Drug (25 mg/kg) % Protection | |
| --- | --- | --- | --- |
| | | Gemfibrozil | Compound 2 |
| Alkaline Phosphatase Heart | 28.81 | 41.2 | 24.0 |
| Ca.-ATPase | 45.51 | 30.2 | 30.2 |
| Glycogen | 20.21 | 32.1 | 25.1 |
| Lipid peroxide | 65.81 | 69.8 | 72.6 |
| Phospholipase | 216.01 | 28.2 | 74.2 |

5.5 Androgenic Activity

The relative affinity of a few selected compounds in the series for cytoplasmic androgenic receptors present in human breast tumour cells MCF-7 (Michigan Cancer Foundation, MCF, USA) was estimated and compared with 4,5-dihydrotestosterone (DHT). The results showed that the compounds 2,3 and 5 have no or only negligible binding affinity which therefore would be a reflection of their low androgenic effect.

5.6 Progestational and Antiprogestational Activity

The relative affinity of compounds for cytoplasmic progesterone receptors present in human breast tumour cells (MCF-7) were estimated and compared with 16-ethyl-21-hydroxy-19-norpregna-4-ene-3,20-dione (Org 2058). The experiments conducted revealed that the compounds 2,3 and 5 have no or only negligible binding affinity.

The progestational activity was also tested in vivo by Clauberg assay method. The degree of endometrial proliferation was estimated on the McPhail scale where 3' or 4' was considered as a full progestational effect. 3β-Hydroxypregna-5,16-dien-20-one (2) did not extent any activity even at 200 mg/kg dose, whereas progesterone showed, as expected marked progestational activity even at 50 mg/kg.

What is claimed is:

1. A method of using compounds represented by the structural formula (I):

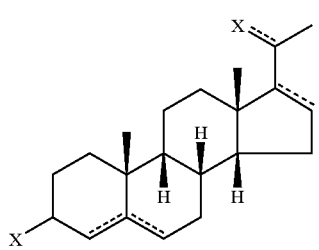

(I)

containing at least one olefinic bond in or on their D-ring for the treatment of hyperlipidemic and hyperglycemic conditions in mammals, said method comprising administering an effective amount of the said compounds to recipient mammals wherein X=OH or O and the olefinic bonds are at 4(5); 5(6); 16(17); or 17(20).

2. A method as claimed in claim 1, wherein the compounds of formula (I) are administered in the form of tablets, capsules, or injectibles.

3. A method as claimed in claim 1, wherein the compounds of formula (I) are characterized as pregnadienones and pregnadienols.

4. A method as claimed in claim 1, wherein the compounds is 3β-hydroxyprena-5,16-dien-20-one, having the following structural formula (II)

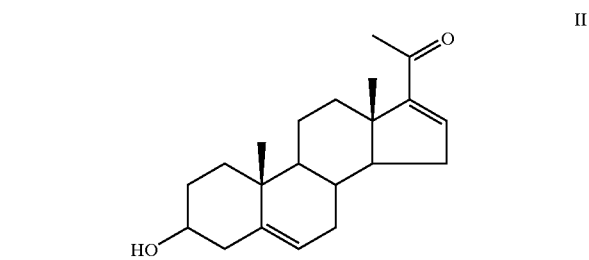

(II)

5. A method as claimed in claim 1, wherein the compounds of formula (I) are optically administered to the recipient mammal as an admixture with conventional anti-platelet, anti-atherosclerotic, hypolipoproteinic, or antidiabetic, drugs.

6. A method as claimed in claim 1 wherein the compounds of formula (I) are essentially free of side effects associated with conventional hyperlipidermic, or hyperglycemic drugs.

7. A method as claimed in claim 1, wherein the compounds of formula (I) exhibit cardioprotective, anti-diabetic, anti-atherosclerotic, or anti-oxidant properties.

8. A method of treatment of hyperlipidemic and hyperglycemic conditions in mammals, which comprises administration to a recipient, a therapeutic composition comprising an effective amount of compound of the following formula (I) with conventional carriers

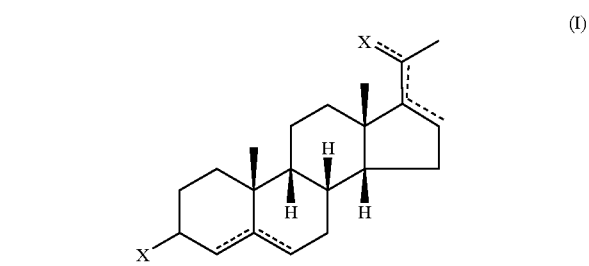

(I)

where X=OH and the olefinic bonds are at 4(5); 5(6); 16(17); or 17(20).

9. A method of treatment as claimed in claim 8, wherein the recipient mammals are human beings, rhesus monkeys, rats, or rabbits.

10. A method of treatment as claimed in claim 8, wherein the conventional carriers are selected from anti-platelet, anti-atherosclerotic, hypolipoproteinic, or anti-diabetic drugs.

11. A method of treatment as claimed in claim 8, wherein the said compounds of formula (I) essentially contain an olefinic bond in or on their D-ring.

12. A method of treatment as claimed in claim 8, wherein the compounds of formula (I) are essentially free of androgenic, progestinal and side effects.

13. A method of treatment as claimed in claim 8, wherein the therapeutic composition is administered in the form of tablets, capsules, or injectibles.

* * * * *